United States Patent
Rose et al.

(10) Patent No.: US 10,864,150 B2
(45) Date of Patent: *Dec. 15, 2020

(54) HAIR TREATMENT PROCESS

(71) Applicant: KAO CORPORATION, Tokyo (JP)

(72) Inventors: Burkhard Rose, Darmstadt (DE); Jonathan Wood, Weinheim (DE); Robert Kussmaul, Weinheim (DE)

(73) Assignee: KAO CORPORATION, Tokyo (JP)

( * ) Notice: Subject to any disclaimer, the term of this patent is extended or adjusted under 35 U.S.C. 154(b) by 297 days.

This patent is subject to a terminal disclaimer.

(21) Appl. No.: 15/022,143

(22) PCT Filed: Sep. 16, 2013

(86) PCT No.: PCT/EP2013/069137
§ 371 (c)(1),
(2) Date: Mar. 15, 2016

(87) PCT Pub. No.: WO2015/036053
PCT Pub. Date: Mar. 19, 2015

(65) Prior Publication Data
US 2016/0235638 A1    Aug. 18, 2016

(51) Int. Cl.
| | |
|---|---|
| *A61Q 5/04* | (2006.01) |
| *A61K 8/365* | (2006.01) |
| *A45D 7/06* | (2006.01) |
| *A45D 20/04* | (2006.01) |
| *A61K 8/31* | (2006.01) |
| *A61K 8/34* | (2006.01) |
| *A61K 8/41* | (2006.01) |
| *A61K 8/73* | (2006.01) |
| *A61K 8/891* | (2006.01) |

(52) U.S. Cl.
CPC .......... *A61K 8/365* (2013.01); *A45D 7/06* (2013.01); *A45D 20/04* (2013.01); *A61K 8/31* (2013.01); *A61K 8/342* (2013.01); *A61K 8/416* (2013.01); *A61K 8/73* (2013.01); *A61K 8/731* (2013.01); *A61K 8/891* (2013.01); *A61Q 5/04* (2013.01); *A61K 2800/30* (2013.01); *A61K 2800/48* (2013.01); *A61K 2800/882* (2013.01)

(58) Field of Classification Search
None
See application file for complete search history.

(56) References Cited

U.S. PATENT DOCUMENTS

| | | | | |
|---|---|---|---|---|
| 9,844,500 B2 * | 12/2017 | Mannozzi | ................ | A45D 7/06 |
| 2006/0222614 A1 * | 10/2006 | Buck | ....................... | A61K 8/604 |
| | | | | 424/70.7 |
| 2010/0172855 A1 * | 7/2010 | Paul | ........................ | A61K 8/44 |
| | | | | 424/70.11 |
| 2010/0300471 A1 * | 12/2010 | Malle | ...................... | A61K 8/362 |
| | | | | 132/204 |
| 2012/0186596 A1 * | 7/2012 | Xavier | ..................... | A45D 7/04 |
| | | | | 132/206 |
| 2015/0305469 A1 * | 10/2015 | Paul | ....................... | A61K 8/342 |
| | | | | 132/206 |

FOREIGN PATENT DOCUMENTS

| | | | | |
|---|---|---|---|---|
| GB | 1 416 564 | | 12/1975 | |
| JP | H02-276824 A | | 11/1990 | |
| WO | WO-2011/104282 A2 | | 9/2011 | |
| WO | WO-2011/104282 A3 | | 9/2011 | |
| WO | WO2012/010351 | * | 1/2012 | |
| WO | WO-2012/010351 A2 | | 1/2012 | |
| WO | WO-2012/010351 A3 | | 1/2012 | |
| WO | WO-2014072645 A1 | * | 5/2014 | .............. A61Q 5/04 |

OTHER PUBLICATIONS

"Studies from the Ortho S.A.Sprague", memorial institute, vol. 9, p. 866 (Year: 1921).*

* cited by examiner

*Primary Examiner* — Jyothsna A Venkat
(74) *Attorney, Agent, or Firm* — Foley & Lardner LLP

(57) ABSTRACT

The present invention a process for straightening the hair, using a composition comprising at least one carboxylic acid of the formula (I): R—CO—COOH Formula (I) The process of the invention is characterized in that it involves the treating of the hair with the composition and the drying of the treated hair under conditions of mechanical tension and hot air flow having a temperature of 60-140° C.

2 Claims, 2 Drawing Sheets

HAIR TREATMENT PROCESS

The present invention relates to a hair treatment process for straightening the hair, reducing frizz or improving the manageability of the hair.

BACKGROUND OF THE INVENTION

A known method for straightening curly or frizzy hair involves the use of straightening irons. The high temperature of the iron leads to a breakage of hydrogen bonds in the keratin of the hair, achieving a temporary straightening. The hydrogen bonds are formed again by the action of moisture, so that the hair reverts back to its original shape over the time because of air humidity, and the straightening effect vanishes after washing the hair.

The shape of the hair is largely determined by the disulfide bonds linking two cysteine moieties of the hair keratin. In order to achieve a more permanent shaping of the hair, known methods involve the cleavage of the disulfide bonds by the action of a sulfide- or thio group containing reducing agent. After the hair has been brought into the desired shape, new disulfide bonds are formed by applying an oxidizing agent such as hydrogen peroxide, thus fixing the shape of the hair. The use of such agents, however, may cause damage to the hair.

As an example for this kind of hair shaping treatment, reference is made to GB 1 416 564, describing reducing compositions comprising thioglycolates or thiolactates as reducing agents and fixing compositions comprising hydrogen peroxide as an oxidizing agent. The reducing compositions may further comprise a salt of an acid such as glyoxylic acid as a buffering agent.

As an alternative to the above-described two-step reduction and oxidation process, the disulfide bridges can be cleaved by the action of an alkaline agent such as sodium hydroxide at a pH of about 11 or higher. Under these conditions, the disulfide (or cystin) moiety can undergo a disproportionation reaction under the elimination of sulfur, and is cleaved into an alpha-beta-unsaturated dehydro-alanine moiety and a cysteine moiety. After the hair has been brought into the desired shape, the dehydro-alanin moieties and the cysteine moieties form thioether bonds and combine to lanthionine, stabilizing the straightened state of the hair. Since the disulfide or cystin moieties are converted into lanthionine moieties, this type of hair straightening process using an alkaline agent is also called lanthionization.

Both the two-stage reduction/oxidation method and the lanthionization method rely on a cleavage of the disulfide bonds and the formation of new bonds among the hair proteins, leading to an irreversible change of the shape of the hair. This means that these processes can achieve a permanent straightening, wherein the treated portion of the hair maintains its shape, and the straightening effect only vanishes because of the growth of the hair.

Recently, it has been found that carboxylic acids having a carbonyl group adjacent to the carboxy group, such as glyoxylic acid, which are known as a buffering agent in cosmetic compositions, may have a semi-permanent straightening effect when used in combination with mechanical straightening means.

In this respect, WO 2011/104282 describes a process for semi-permanent hair straightening, which involves applying a composition comprising an α-keto acid onto the hair, leaving the composition in contact with the hair for 15 to 120 minutes, drying the hair and straightening the hair with a straightening iron at a temperature of 200±50° C.

Furthermore, WO 2012/010351 describes a treatment for semi-permanent straightening of curly, frizzy or wavy hair by applying a solution of glyoxylic acid in combination with mechanical straightening, using a straightening iron at a temperature of 200±30° C. After the treatment, the hair is said to retain its shape for at least six consecutive washings.

The previously described methods utilizing an alpha-keto acid such as glyoxylic acid, however, require the use of a straightening iron in order to achieve the hair straightening effect. The high temperature of the straightening iron promotes the cross-linking action of the alpha-keto acid and thus leads to a semipermanent hair straightening.

Straightening methods utilizing an alpha-keto acid which do not use an iron have not yet been described in the prior art.

SUMMARY OF THE INVENTION

The present invention thus relates to a process for treating hair, characterized in that it comprises the following steps performed in this order:
(a) application of a hair straightening composition having a pH of 4 or less and comprising at least one carboxylic acid of the formula (I) and/or a hydrate thereof and/or a salt thereof onto the hair:

R—CO—COOH                     Formula (I)

wherein R is selected from hydrogen, COOH, CN, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{10}$ cycloalkyl, optionally substituted $C_1$-$C_{10}$ aryl or a 5-10-membered, optionally substituted heteroaryl group, wherein the optional substituents of the alkyl group are selected from halogen, hydroxyl, amino and $C_1$-$C_4$ alkoxy, and the optional substituents of the other groups are selected from halogen, hydroxyl, amino, $C_1$-$C_4$ alkyl and $C_1$-$C_4$ alkoxy,
(b) leaving the composition on the hair for 1 to 120 minutes;
(c) optionally rinsing off the hair;
(d) drying the hair under conditions of mechanical tension and hot air flow, so that the temperature on the hair is 60-140° C.; and
(e) optionally rinsing off and/or shampooing the hair.

DETAILED DESCRIPTION OF THE INVENTION

Figure 1A:
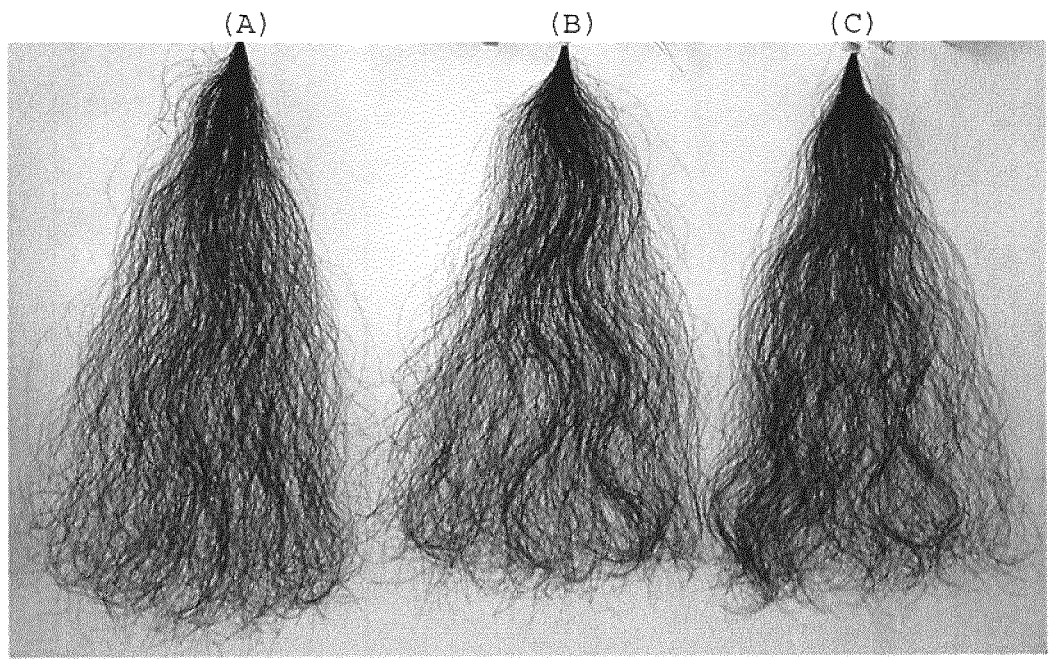
FIGS. 1A and 1B show samples of hair before and after the following treatments:
(A) Application of the straightening composition, drying without mechanical tension, shampooing (Reference);
(B) Application of the straightening composition, drying and application of a straightening iron, shampooing (Reference)
(C) Application of the straightening composition, drying under mechanical tension, shampooing (Example of the present Invention)

Hair straightening methods utilizing a carboxylic acid of Formula (I) such as glyoxylic acid in combination with straightening iron treatment are time consuming. These methods often take at least 90 to 120 minutes, wherein the ironing is the main time consuming step, accounting for about 30 to 60 minutes, depending on the hair length. Thus, there is need for a hair straightening method which is less time consuming and does not require the use of a straightening iron.

Previously, it was believed that for hair straightening by treatment with a carboxylic acid of Formula (I) as described above, the ironing is necessary in order to provide a sufficiently high temperature for achieving a cross-linking of the hair.

The present inventors unexpectedly found that the use of an iron is not necessary. Surprisingly, a remarkable straightening effect is already achieved by imparting mechanical tension to the hair and drying the hair with a blow dryer. The process of the present invention makes use of this finding and thus can provide a semi-permanent straightening of the hair in a much more time-efficient manner, since the time consuming application of the straightening iron is avoided. Besides, the use of a hot air stream is milder than a straightening iron treatment, so that the process of the present invention also provides the benefit that the risk of hair damage is decreased.

1. The Carboxylic Acid of Formula (I)

The straightening composition comprises at least one carboxylic acid of the following formula (I) as the active component for achieving the straightening effect:

R—CO—COOH    Formula (I)

wherein R is selected from hydrogen, COOH, CN, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{10}$ cycloalkyl, optionally substituted $C_6$-$C_{10}$ aryl or a 5-10-membered, optionally substituted heteroaryl group, wherein the optional substituents of the alkyl group are selected from halogen, hydroxyl, amino and $C_1$-$C_4$ alkoxy, and the optional substituents of the other groups are selected from halogen, hydroxyl, amino, $C_1$-$C_4$ alkyl and $C_1$-$C_4$ alkoxy.

As preferred examples, glyoxylic acid, pyruvic acid and 2-ketobutyric acid can be mentioned.

The carboxylic acid of Formula (I) may be comprised in the composition in its free acid form. The carbonyl group adjacent to the acid group of the acid may also be present in the hydrate form. Apart from the free acid form and the hydrate thereof, salts of the acid or the hydrate may also be used.

The hydrate of the acid of Formula (I) may be formed when providing the composition as an aqueous solution. For instance, glyoxylic acid (H—CO—COOH) in aqueous solution is almost quantitatively present as the hydrate (H—C(OH)$_2$—COOH). Besides, the hydrate may also condense to dimers.

A salt of the carboxylic acid of Formula (I) may also be used. As examples, alkali metal salts such as the sodium or potassium salt, alkaline earth metal salts such as the magnesium salt or the calcium salt and tertiary or quaternary ammonium salts may be mentioned.

In the present invention, glyoxylic acid, its salts and its hydrated form are the more preferred carboxylic acids of Formula (I).

The concentration of the at least one carboxylic acid of the Formula (I) and/or a hydrate thereof and/or salts thereof is in the range of 0.1 to 40%, preferably 0.5 to 30%, more preferably 1.0 to 25% and more preferably 2.5 to 20%, and even more preferably 2.5 to 14% by weight, based on the total weight of the straightening composition.

2. Surfactant

The straightening composition may comprise a surfactant. As the surfactant, any of a cationic surfactant, a nonionic surfactant, an amphoteric surfactant and an anionic surfactant can be used. It is also possible to use two or more types of surfactants in combination.

The cationic surfactant is preferably a mono-long chain alkyl quaternary ammonium salt, having a $C_8$-$C_{24}$ alkyl residue and three $C_1$-$C_4$ alkyl residues, a di-long chain alkyl quaternary ammonium salt having two $C_3$-$C_{24}$ alkyl residues and two $C_1$-$C_4$ alkyl residues, or a mixture thereof.

Preferably at least one mono alkyl quaternary ammonium surfactant is selected from the compounds with the general formula

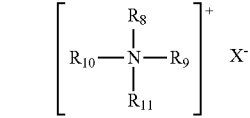

$$\left[ \begin{array}{c} R_8 \\ | \\ R_{10}—N—R_9 \\ | \\ R_{11} \end{array} \right]^+ X^-$$

wherein $R_8$ is a saturated or unsaturated, branched or straight alkyl chain with 8-22 C atoms or

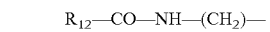

$R_{12}$—CO—NH—(CH$_2$)— wherein $R_{12}$ is a saturated or unsaturated, branched or straight alkyl chain with 7-21 C atoms and n is an integer of 1-4, or

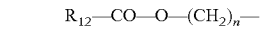

$R_{12}$—CO—O—(CH$_2$)$_n$— wherein $R_{12}$ is a saturated or unsaturated, branched or straight alkyl chain with 7-21 C atoms and n is an integer of 1-4, and $R_9$, $R_{10}$ and $R_{11}$ are independent from each other an alkyl group with 1 to 4 carbon atoms, hydroxyl alky chain with 1 to 4 carbon atoms, or ethoxy or propoxy group with a number of ethoxy or propoxy groups varying in the range of 1 to 4, and X is chloride, bromide, methosulfate or ethosulfate.

Suitable cationic surfactants are, for example, long-chain quaternary ammonium compounds which can be used alone or in admixture with one another, such as cetyl trimethyl ammonium chloride, myristyl trimethyl ammonium chloride, behentrimonium chloride, trimethyl cetyl ammonium bromide, stearyl trimethyl ammonium chloride, stearyl trimonium chloride and stearamidopropyltrimonium chloride.

Examples of the dialkyl quaternary ammonium salt include compounds of the formula

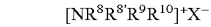

[NR$^8$R$^{8'}$R$^9$R$^{10}$]$^+$X$^-$ wherein R$^8$, R$^9$, R$^{10}$ and X are the same as defined above for the monoalkyl quaternary ammonium compound and R$^{8'}$ is selected from the same groups as defined for R$^8$. R$^8$ and R$^{8'}$ may be identical or different. Alternatively, R$^8$ and R$^{8'}$ may be linked to each other to form a heterocyclic ring.

Examples for the dialkyl quaternary ammonium compound include di-$C_{12}$-$C_{15}$-alkyl dimethylammonium or di-$C_{12}$-$C_{15}$-alkyl hydroxyethylmonium methylsulfonate and dioleylethyl hydroxyethylmonium methosulfate (TETPRANYL™ CO-40, commercially available from KAO CORPORATION). Examples where R$^8$ and R$^{8'}$ are cyclized include imidazoline type surfactants such as Quaternium-91 (di-behenyl imidazoline quat, methosulfate salt).

The monoalkyl and the dialkyl quaternary ammonium compounds may be used in admixture, preferably at a ratio within the range of 5:1 to 1:5. As an example for such a mixture, the commercially available product Crodazosoft™

DBP-Q (manufactured by Croda Inc.) may be mentioned, which is mixture of Quaternium-91, cetrimonium methosulfate and cetearyl alcohol.

Examples of the nonionic surfactant include polyoxy-$C_{1-4}$-alkylene $C_{8-24}$-alkyl ether, polyoxy-$C_{1-4}$-alkylene $C_{8-24}$-alkylene alkenyl ether, higher ($C_{12}$-$C_{24}$) fatty acid sucrose ester, polyglycerin $C_{8-24}$-fatty acid ester, higher ($C_{12}$-$C_{24}$) fatty acid mono- or diethanolamide, polyoxyethylene hardened castor oil, polyoxyethylene sorbitan $C_{8-24}$-fatty acid ester, polyoxyethylene sorbit $C_{8-24}$-fatty acid ester, $C_{8-24}$-alkyl saccharide surfactant, $C_{8-24}$-alkylamine oxide, and $C_{8-24}$-alkylamidoamine oxide.

Examples of the amphoteric surfactant include an imidazoline-based surfactant, a carbobetaine-based surfactant, an amidobetaine-based surfactant, a sulfobetaine-based surfactant, a hydroxysulfobetaine-based surfactant and an amidosulfobetaine-based surfactant.

Examples of the anionic surfactant include alkylbenzenesulfonate, alkyl or alkenyl ether sulfate, alkyl or alkenyl sulfate, olefin sulfonate, alkanesulfonate, saturated or unsaturated fatty acid salts, alkyl or alkenyl ether carboxylate, α-sulfo fatty acid salts, N-acylamino acid type surfactants, phosphoric acid mono- or diester type surfactants, and sulfosuccinate. Examples of the alkyl ether sulfate include polyoxyethylene alkyl ether sulfate. Examples of the counterion for the anionic residues of these surfactants include an alkalimetal ion such as sodium ion or potassium ion; an alkaline earth metal ion such as calcium ion or magnesium ion; an ammonium ion; and an alkanolamine having 1 to 3 alkanol groups each having 2 or 3 carbon atoms (for example, monoethanolamine, diethanolamine, triethanolamine, or triisopropanolamine).

The surfactant can be used singly or in combination of two or more kinds. When adding a surfactant to the straightening composition, the content thereof usually is 0.05 to 10% wt. %, more preferably 0.1 to 5 wt. %, based on the total weight of the straightening composition.

4. Conditioning Component

The straightening composition may optionally comprise a conditioning component suitable for application to the hair. The conditioning component is an oil or polymer which adheres to the hair and improves the feel and the manageability.

When using the conditioning component, the total content thereof is preferably 0.01 to 30 wt. %, more preferably 0.05 to 20 wt. %, and even more preferably 0.1% to 10 wt. %, based on the total weight of the straightening composition.

Examples of the conditioning component generally include cationic polymers, silicones, higher alcohols, and organic conditioning oils (for example, hydrocarbon oil, polyolefin and fatty acid ester). The composition may comprise a single type of conditioning component, or two or more in combination.

Cationic Polymers

A cationic polymer is a polymer having a cationic group or a group capable of being ionized into a cationic group, and in general, an amphoteric polymer acquiring net cationic charge is also included in the terminology. That is, the cationic polymer is a polymer containing an amino group or an ammonium group in a side chain of the polymer chain, or a polymer including a diallyl quaternary ammonium salt as a constituent unit, and examples thereof include cationized cellulose, cationic starch, cationic guar gum, a polymer or copolymer of a diallyl quaternary ammonium salt, and quaternized polyvinylpyrrolidone. Among these, from the viewpoint of softness, smoothness and easy finger-combing during shampooing, and easy manageability and moisture retention during drying, and from the viewpoint of stability of the agent, a polymer including a diallyl quaternary ammonium salt as a constituent unit, quaternized polyvinylpyrrolidone, and cationized cellulose are preferred, and a polymer or copolymer of a diallyl quaternary ammonium salt, and cationized cellulose are more preferred.

Specific examples of the polymer or copolymer of a diallyl quaternary ammonium salt include dimethyldiallylammonium chloride polymer (polyquaternium-6, for example, MERQUAT 100; Nalco Company), dimethyldiallylammonium chloride/acrylic acid copolymer (polyquaternium-22, for example, MERQUAT 280, MERQUAT 295; Nalco Company), and dimethyldiallylammonium chloride/acrylic acid amide copolymer (polyquaternium-7, for example, MERQUAT 550; Nalco Company).

Specific examples of the quaternized polyvinylpyrrolidone include quaternary ammonium salts synthesized from a copolymer of vinylpyrrolidone (VP) and dimethylaminoethyl methacrylate, and diethyl sulfate (polyquaternium 11, for example, GAFQUAT 734, GAFQUAT 755 and GAFQUAT 755N (all by ISP Japan, Ltd.)).

Specific examples of the cationized cellulose include a polymer of a quaternary ammonium salt obtained by adding glycidyltrimethylammonium chloride to hydroxyethylcellulose (polyquaternium-10, for example, RHEOGUARD G and RHEOGUARD GP (all by Lion Corp.), POLYMER JR-125, POLYMER JR-400, POLYMER JR-30M, POLYMER LR-400 and POLYMER LR-30M (all by Amerchol Corp.)), and a hydroxyethylcellulose/dimethyldiallylammonium chloride copolymer (polyquaternium-4, for example, CELQUAT H-100, CELQUAT L-200 (all by National Starch and Chemical Company)).

The cationic polymer may be used in combination of two or more kinds. Furthermore, the cationic polymer gives better effects when the content is increased, but an excessively high content of the cationic polymer may cause stability failure and a decrease in the viscosity of the agent alone or during mixing. From this viewpoint, and from the viewpoint of enhancing the feel to the touch, the content of the cationic polymer is preferably 0.001 to 20 wt %, more preferably 0.01 to 10 wt. %, and even more preferably 0.05 to 5 wt. %, based on the total weight of the straightening composition.

Silicones

In order to improve the feel of use, the straightening composition preferably contains a silicone. Examples of the silicone include dimethylpolysiloxane, and modified silicone (for example, amino-modified silicone, fluorine-modified silicone, alcohol-modified silicone, polyether-modified silicone, epoxy-modified silicone, polyoxazoline silicone (as described in JP Hei 2-276824), or alkyl-modified silicone), but dimethylpolysiloxane, polyether-modified silicone and amino-modified silicone are preferred.

The dimethylpolysiloxane may be any cyclic or non-cyclic dimethylsiloxane polymer, and examples thereof include SH200 series, BY22-019, BY22-020, BY11-026, B22-029, BY22-034, BY22-050A, BY22-055, BY22-060, BY22-083, FZ-4188 (all by Dow Corning Toray Co., Ltd.), KF-9008, KM-900 series, MK-15H, and MK-88 (all by Shin-Etsu Chemical Co., Ltd.).

The polyether-modified silicone may be any silicone having a polyoxyalkylene group, and the group constituting the polyoxyalkylene group may be an oxyethylene group or an oxypropylene group. More specific examples include KF-6015, KF-945A, KF-6005, KF-6009, KF-6013, KF-6019, KF-6029, KF-6017, KF-6043, KF-353A, KF-354A, KF-355A (all by Shin-Etsu Chemical Co., Ltd.), FZ-2404, SS-2805, FZ-2411, FZ-2412, SH3771M, SH3772M, SH3773M, SH3775M, SH3749, SS-280X series, BY22-008 M, BY11-030, and BY25-337 (all by Dow Corning Toray Co., Ltd.).

The amino-modified silicone may be any silicone having an amino group or an ammonium group, and examples thereof include an amino-modified silicone oil having all or a part of the terminal hydroxyl groups capped with a methyl group or the like, and an amodimethicone which does not have the terminals capped. A preferred example of the amino-modified silicone may be a compound represented by the following formula:

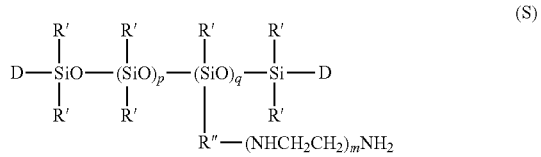

(S)

wherein R' represents a hydroxyl group, a hydrogen atom or $R^X$; $R^X$ represents a substituted or unsubstituted monovalent hydrocarbon group having 1 to 20 carbon atoms; D represents $R^X$, R"—$(NHCH_2CH_2)_m NH_2$, $OR^X$, or a hydroxyl group; R" represents a divalent hydrocarbon group having 1 to 8 carbon atoms; m represents a number from 0 to 3; p and q represent numbers, the sum of which is, as a number average, equal to or greater than 10 and less than 20,000, preferably equal to or greater than 20 and less than 3000, more preferably equal to or greater than 30 and less than 1000, and even more preferably equal to or greater than 40 and less than 800.

Specific examples of suitable commercially available products of the amino-modified silicone include amino-modified silicone oils such as SF8452C, SS-3551 (all by Dow Corning Toray Co., Ltd.), KF-8004, KF-867S, and KF-8015 (all by Shin-Etsu Chemical Co., Ltd.); and amodimethicone emulsions such as SM8704C, SM8904, BY22-079, FZ-4671, and FZ-4672 (all by Dow corning Toray Co., Ltd.).

The total content of these silicones in the straightening composition of the present invention is usually 0.1 to 20 wt. %, preferably 0.2% to 10 wt. % and more preferably 0.5 to 5 wt. %, based on the total weight of the straightening composition.

Oil Component

For improving the feel upon use, the straightening composition may also include an organic conditioning oil.

The organic conditioning oil that is suitably used as a conditioning component is preferably a low-viscosity and water-insoluble liquid, and is selected from a hydrocarbon oil having at least 10 carbon atoms, a polyolefin, a fatty acid ester, a fatty acid amide, a polyalkylene glycol, and mixtures thereof. The viscosity of such an organic conditioning oil as measured at 40° C. is preferably 1 to 200 mPa·s, more preferably 1 to 100 mPa·s, and even more preferably 2 to 50 mPa·s. For the determination of the viscosity, a capillary viscometer may be used.

Examples of the hydrocarbon oil include a cyclic hydrocarbon, a linear aliphatic hydrocarbon (saturated or unsaturated), and a branched aliphatic hydrocarbon (saturated or unsaturated), and polymers or mixtures thereof are also included. The linear hydrocarbon oil preferably has 12 to 19 carbon atoms. The branched hydrocarbon oil includes hydrocarbon polymers, and preferably has more than 19 carbon atoms.

The polyolefin is a liquid polyolefin, more preferably a liquid poly-α-olefin, and even more preferably a hydrogenated liquid poly-α-olefin. The polyolefin used herein is prepared by polymerizing an olefin monomer having 4 to 14 carbon atoms, and preferably 6 to 12 carbon atoms.

The fatty acid ester may be, for example, a fatty acid ester having at least 10 carbon atoms. Examples of such a fatty acid ester include esters having a hydrocarbon chain derived from a fatty acid and an alcohol (for example, monoesters, polyhydric alcohol esters, or di- and tricarboxylic acid esters). The hydrocarbon group of these fatty acid esters may have another compatible functional group such as an amide group or an alkoxy group as a substituent, or the hydrocarbon group may be covalently bonded to those functional groups. More specifically, an alkyl and alkenyl ester of a fatty acid having a fatty acid chain having 10 to 22 carbon atoms, a carboxylic acid ester of an aliphatic alcohol having an aliphatic chain derived from an alkyl and/or alkenyl alcohol having 10 to 22 carbon atoms, and a mixture thereof are suitably used. Specific examples of these preferred fatty acid esters include isopropyl isostearate, hexyl laurate, isohexyl laurate, isohexyl palmitate, isopropyl palmitate, isopropyl myristate, decyl oleate, isodecyl oleate, hexadecyl stearate, decyl stearate, dihexadecyl adipate, lauryl lactate, myristyl lactate, cetyl lactate, oleyl stearate, oleyl oleate, oleyl myristate, lauryl acetate, cetyl propionate and dioleyl adipate.

Further suitable oil components are natural oils such as paraffin oil and natural triglycerides.

Suitable natural triglycerides are argan oil, shea butter oil, karite oil, olive oil, almond oil, avocado oil, ricinus oil, coconut oil, palm oil, sesame oil, peanut oil, sunflower oil, peach kernel oil, wheat germ oil, macadamia nut oil, macadamia oil, night primrose oil, jojoba oil, castor oil, soya oil, lanolin, passiflora oil, black cumin oil, borage oils, rapeseed oil, hempseed oil, kukui nut oil, and rosehip oil.

The organic conditioning oil may be used in combination of two or more kinds, and the total concentration is typically in the range of 0.1 to 20 wt. %, preferably 0.2 to 10 wt. %, more preferably 0.5 to 5 wt. %, based on the total weight of the straightening composition.

Alcohols

From the viewpoint of improving the sense of touch and stability, the straightening composition may also contain a higher alcohol having 8 carbon atoms or more. Usually, the higher alcohol has 8 to 24 carbon atoms, and preferably 16 to 22 carbon atoms. Specific examples thereof include cetyl alcohol, stearyl alcohol, behenyl alcohol, and mixtures thereof.

The higher alcohol may be used in combination of two or more kinds, and the content thereof is typically 0.1 to 20 wt. %, preferably 0.2 to 10 wt. %, more preferably 0.5 to 5 wt. %, based on the total weight of the straightening composition.

Additionally polyols may suitably be comprised in the compositions. Examples of the polyalkylene glycol include polyethylene glycol and polypropylene glycol, and a mixture of the two may be used, or a copolymer of ethylene oxide and propylene oxide may also be used.

4. The Formulation of the Straightening Composition

The straightening composition may suitably be in the form of a solution, emulsion, cream, gel, paste and mousse.

In order to provide a sufficient straightening effect, the pH of the straightening composition is 4.0 or less, preferably in the range of 1 to 3.5, more preferably 1.0 to 3.0 and more preferably 1.5 to 2.5, as measured directly and at ambient temperature (25° C.). The pH of the composition may be adjusted using known alkaline solutions, preferably with sodium hydroxide solution.

As discussed above, conventional permanent hair shaping/straightening techniques are based on the re-organization of the disulfide bridges and involve a cleavage of the disulfide bonds either by using a sulfur-based reducing agent or an alkali agent, followed by the shaping of the hair and the formation of new bonds (i.e., disulfide bonds formed by the action of an oxidizing agent or thioether bonds, respectively). In contrast to these permanent straightening methods, the present invention does not utilize cleavage of the disulfide bonds and fixing the bonds in the new shape. Therefore, the straightening composition of the present invention does not require the presence of sulfur-based reducing agents. However, up to 2% by weight calculated to the total of the composition of sulfur based reducing agents does not disturb the straightening performance of the compositions. Therefore, the treatment composition has less than 2% by weight of sulfur-based reducing agents, and preferably is free of sulfur-based reducing agents.

Emulsion

The straightening composition is preferably formulated as an emulsion, preferably including a fatty alcohol such as cetearyl alcohol. In view of emulsion stability, a non-ionic or a cationic surfactant may optionally be added.

In order to improve the ease of use, one or more further conditioning components such as a silicone, preferably an amodimethicone may be added to the emulsion.

Gel Emulsion

It is also preferable to formulate the composition as a gel emulsion. This may be accomplished by adding a polymeric thickening agent to the emulsion formulation. Preferable polymeric thickening agents include anionic polysaccharides such as alginate, pectinate, xanthan, hydroxypropyl xanthan or dehydroxanthan, non-ionic polysaccharides such as cellulose ethers (e.g., methylcellulose, hydroxyethylcellulose (HEC), methyl hydroxyethylcellulose (MHEC), ethyl hydroxyethylcellulose (EHEC), methyl ethyl hydroxyethylcellulose (MEHEC)), starch or dextrins, and cationic or amphoteric polymers such polyquaternium-37 or the ones described above as conditioning agents. Among these polymers, xanthan, hydroxypropyl xanthan and dehydroxanthan are especially preferable.

The viscosity of such gel emulsions is typically within the range of 1,000 to 25,000, preferably 2500 to 15,000 mPa*s, as measured at 20° C. with a Brookfield viscometer (e.g., at 10 rpm with an appropriated spindle). The concentration of the polymeric thickening agent depends on the type of the agent and the desired viscosity, and is typically within the range of 0.01 to 15 wt. %, preferably 0.05 to 10 wt. %, more preferably 0.1 to 5 wt. %, and even more preferably 0.5 to 2 wt. % based on the weight of the straightening composition.

Two-Component Formulations

In case it is desired to include compounds such as fragrances or surfactants and/or conditioning components which comprise acid-sensitive groups, it is possible that the storage stability at the above-described pH values is diminished. Besides, it is also possible that fragrance compounds undergo undesired reactions with the carbonyl group of the carboxylic acid of formula (I), which may lower the storage stability.

In order to avoid such problems, it may be preferable in these cases to formulate the straightening composition as a two-part system, comprising the parts A and B, which are stored separately and mixed prior to the application to the hair.

Part A comprises the carboxylic acid of the formula (I), while part B comprises at least one of a fragrance, a surfactant and a conditioning agent. Acid insensitive surfactants, conditioning agents and other components such as thickeners may be added to part A, to part B or to both parts.

The pH of part B is adjusted such that the ingredients have sufficient storage stability, typically above 4 and usually within the range of 4 to 8, while the pH of part A is less than 4, usually within the range of 1 to 3.5. The final pH after mixing of parts A and B is 4 or lower, preferably 1 to 3.5. The parts A and B are mixed at a predefined ratio, e.g., 1:1, prior to use.

5. Hair Treatment Process

The straightening treatment process of the present invention utilizes the acid of formula (I) such as glyoxylic acid as the active agent for providing the straightening effect. The straightening effect is not achieved by cleaving the disulfide bonds by reduction or the action of strong alkali. Accordingly, the usage of a reducing composition or an alkaline relaxer (lanthionization agent) is not required.

In step (a), the straightening composition is applied to the optionally pre-shampooed hair. The application weight ratio of hair to composition is 0.5:2 to 2:0.5, preferably 0.5:1 to 1:0.5, more preferably about 1:1.

Subsequent to the application, the straightening composition is left on the hair for 1 to 120 minutes, preferably 5 to 90 minutes, more preferably 10 to 60 minutes and yet more preferably 15 to 45 minutes at a temperature of 45° C. or below, preferably at ambient temperature (step (b)). Then, the straightening composition may optionally be rinsed off from hair (step (c)).

In subsequent step (d), the hair is dried under the conditions of mechanical tension and hot air flow, so that the temperature on the hair is 60-140° C. In order to provide a good straightening effect, the temperature is preferably 70° C. or higher, more preferably 80° C. or higher, even more preferably 90° C. or higher. Usually, the temperature is 130° C. or less, preferably 110° C. or less. A typically preferable temperature range is 80-130° C., more preferably 90 to 110° C. The drying may be performed with a hair dryer. These temperature values refer to the temperature caused by the hot air stream on the hair. Conveniently, the temperature can be determined in a contact-less thermal radiation measurement, e.g., by capturing the area where the hot air stream comes into contact with the hair with a thermal radiation detector such as an infrared thermometer.

For instance, the measurement may be performed conveniently by pointing the infrared thermometer at the area where the air stream comes into contact with the hair, from a distance such that the target area is appropriately captured (typically about 20 to 40 cm). A usual infrared thermometer ("Temperature Gun") is equipped with means such as a LED or a laser pointer for illuminating the capture area ("spot area"), which facilitates the measurement Drying under conditions of mechanical tension means that mechanical tension is applied either along the whole length of the strand of hair to be dried, or along the part of the strand exposed to the hot air stream.

The mechanical tension during the drying may be applied to the hair continuously by holding a part or the whole of the strand in an elongated state while applying the hot air flow to the strand or the elongated part thereof. It is also possible to apply the tension intermittently, e.g., by continuous combing of the strand with a comb while applying the hot air stream.

For instance, step (d) may be carried out by fixing a hair strand in an elongated state with a tool such as tongs or a round brush and applying a stream of hot air to the elongated strand with a hair dryer.

After the drying, the hair may optionally be rinsed and/or shampooed (step (e)).

EXAMPLES

The present invention will now be illustrated by the following non-limiting Test Examples and Formulation Examples.

Test Example 1

Impact of Tension

Three samples A-C of frizzy hair (bundles of 2 g Indian frizz hair, untreated, obtained from IHIP, International Hair Importers & Products, NY; see FIG. 1A) were shampooed, rinsed off with water and dried at ambient temperature.

Then, an aqueous solution of 10 wt. % glyoxylic acid (pH 1.5, adjusted with NaOH) was applied to the samples A-C at a ratio of hair to solution of 1:1, uniformly distributed with a comb and left on the hair for 15 minutes at 40° C.

Then, the samples were dried with a hair drier at a temperature of 90-100° C. for 10 minutes. The temperature was measured by holding an infrared thermometer at a distance of about 20 to 40 cm from the hair and scanning the area where the air stream comes into contact with the hair. The average of at least ten readings is then taken as the temperature.

Figure 1B:
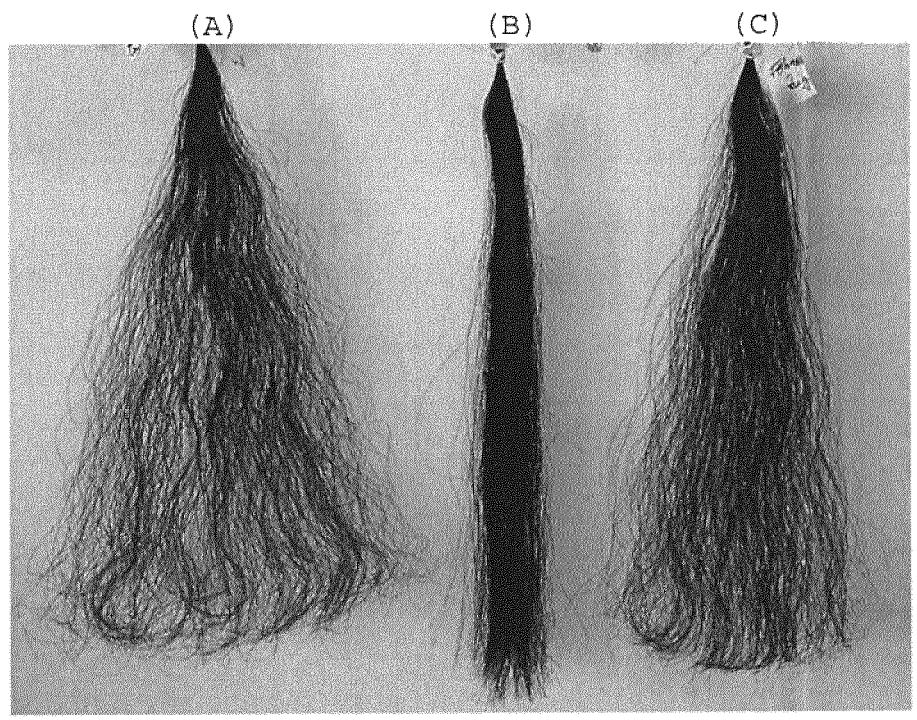

Samples A and B (Reference) were dried in the absence of mechanical tension and serve as reference samples. To sample C, mechanical tension was applied by fixing one end and holding the sample in an elongated state using a round brush. Reference sample B was subsequently treated with a straightening iron at a temperature of 230° C. The samples A-C were rinsed off with water, shampooed, combed and dried at ambient temperature. The result is shown in FIG. 1B.

As apparent, sample C, which has been treated according to the present invention, exhibits a remarkable straightened appearance and reduced frizz in comparison to sample A, even though it has not been treated with an iron like sample B.

This shows that a straightening of the hair with glyoxylic acid is not only achieved by applying a straightening iron at high temperature (Sample B), but also by drying the hair under mechanical tension with a hair dryer in accordance with the present invention (Sample C). Drying the hair in the relaxed state does not lead to a substantial straightening, though (Sample A).

Test Example 2

Impact of Temperature

Figure 2:
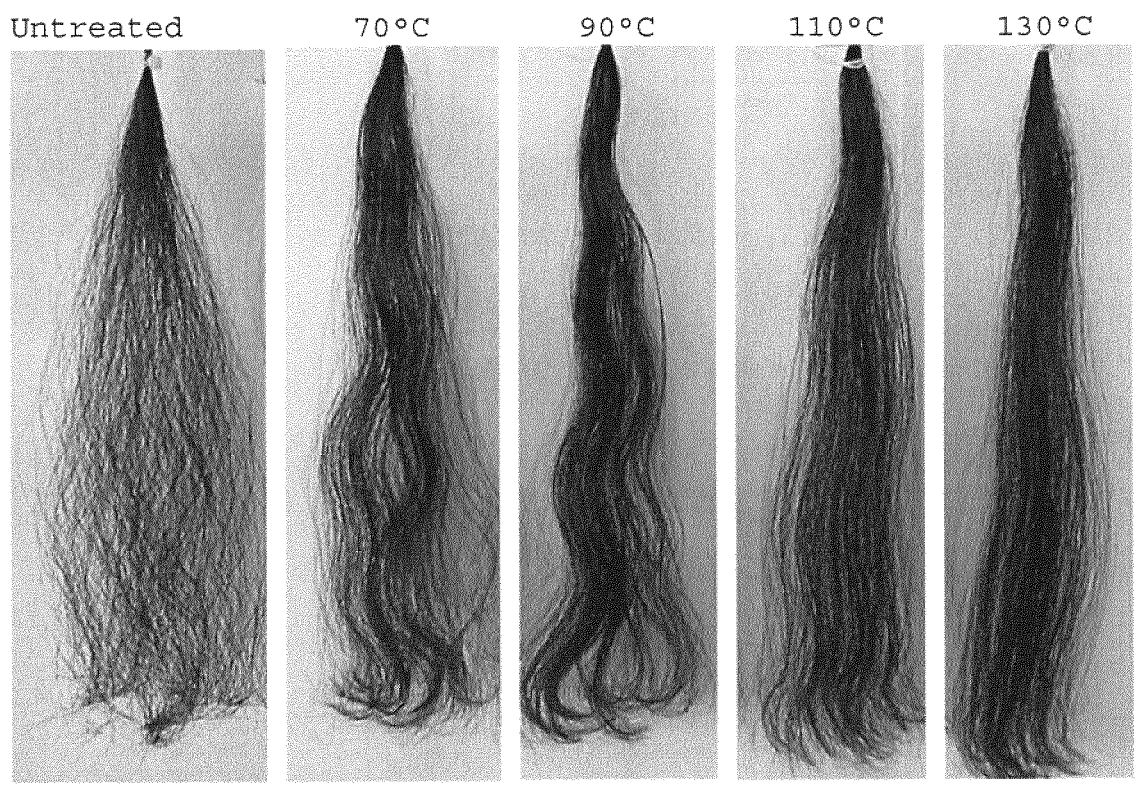
FIG. 2 shows samples of hair treated with the straightening composition, dried under mechanical tension at different temperatures, and shampooed.

Four samples of frizzy hair (bundles of 2 g Indian frizz hair, untreated, obtained from IHIP, International Hair Importers & Products, NY, see leftmost photograph in FIG. 2) were shampooed, rinsed off with water and dried at ambient temperature.

Then, a straightening composition was prepared by mixing the following parts A and B of a two-part gel emulsion at a weight ratio of 1:1.

Part A: Care Emulsion

| | |
|---|---|
| Cetearyl alcohol[1] | 2 wt. % |
| Silicone emulsion[2] | 4 wt. % |
| Behentrimonium Chloride[3] | 0.5 wt. % |
| CrodazosoftTM DBQ-PA[4] | 0.5 wt. % |
| Water | ad 100 wt. % |

[1]Lanette ™ O, available
[2]949 cationic emulsion, available from Dow Corning
[3]Genamin BTLF, available from Clariant
[4]Mixture of Quaternium-91, cetrimonium methosulfate and cetearyl alcohol, available from Croda, Inc.

Part B: Straightening Gel

| | |
|---|---|
| Glyoxylic acid monohydrate[1] | 26.6% |
| NaOH 32% | 3.0% |
| Dehydroxanthan Gum[2] | 0.7% |
| Water | ad 100 wt. % |

[1]corresponding to 20 wt. % free glyoxylic acid
[2]Amaze XT, available from AkzoNobel The mixture, which had a pH of 1.5, was applied to the samples in a ratio of hair to mixture of 1:1, uniformly distributed with a brush and left on the hair for 15 minutes at 40° C. Then, the samples were subjected to mechanical tension using a round brush, and dried in hot air streams having temperatures of 70° C., 90° C., 110° C. and 130° C., respectively.

Then the samples were shampooed, rinsed, combed and air dried at room temperature. This shampooing cycle was repeated after 24 hours. The results are shown in FIG. 2 (the second to fifth photograph show the samples treated with an air stream temperature 70° C., 90° C., 110° C. and 130° C., respectively.

As apparent from the figure, the samples dried at 70 and 90° C. already show a reduced frizziness and a less wavy appearance after two shampooing cycles. The samples dried at 110° C. and 130° C. exhibit a remarkably straightened appearance.

Formulation Examples

Straightening compositions useful for the process of the present invention are described in the following.

Formulation Example 1

| | % by weight |
|---|---|
| Cetearyl alcohol | 5.0 |
| Cetrimonium chloride | 1.0 |
| Ceteareth-20 | 1.0 |
| Dimethicone | 1.0 |
| Distearyldimethylammonium chloride | 1.0 |
| Glyoxylic acid | 5.0 |
| Polyquaternium-37 | 0.5 |
| Water | to 100 |

The pH of the composition is 1.6.

Formulation Example 2

|  | % by weight |
|---|---|
| Cetearyl alcohol | 3.0 |
| Ceteareth-20 | 2.0 |
| Paraffin oil | 1.0 |
| Dibehenyldimonium methosulfate | 0.5 |
| Glyoxylic acid | 5.0 |
| Hydroxyethylcellulose | 1.0 |
| Water | to 100 | pH of the composition is 1.9.

Formulation Example 3

|  | % by weight |
|---|---|
| Cetearyl alcohol | 4.0 |
| Ceteareth-30 | 2.5 |
| Paraffin oil | 0.5 |
| Dimethicone | 0.5 |
| Glyoxylic acid | 5.0 |
| Xanthan gum | 1.0 |
| Water | to 100 |

The pH of the composition is 1.6.

Formulation Example 4

|  | % by weight |
|---|---|
| Cetearyl alcohol | 4.0 |
| Ceteareth-30 | 2.5 |
| Paraffin oil | 0.5 |
| Dimethicone | 0.5 |
| Quaternium-80 | 0.2 |
| Behentrimonium chloride | 0.2 |
| Dicetyldimonium chloride | 0.2 |
| Glyoxylic acid | 5.0 |
| Polyquaternium-22 | 0.5 |
| Water | to 100 |

The pH of the composition is 1.6.

The invention claimed is:

1. Process for straightening hair, comprising the following steps performed in this order:
    (a) application of a hair straightening composition having a pH of 1 to 3 and comprising glyoxylic acid glyoxylic acid is from 2.5% to 14% by weight of the hair straightening composition;
    (b) leaving the composition on the hair for 15 to 45 minutes;
    (c) optionally rinsing off the hair;
    (d) drying the hair under conditions of mechanical tension and hot air flow, so that the temperature on the hair is 80-130° C.; and
    (e) optionally rinsing off and/or shampooing the hair,
    wherein the hair straightening composition does not comprise a reducing composition and an alkaline relaxer, wherein the hair straightening composition is a gel, and wherein the hair straightening composition comprises 0.5-2% of polymeric thickening agents selected from the group consisting of, xanthan gum, dehydroxanthan gum and hydroxypropyl xanthan and wherein step (d) is performed by holding a hair strand fixed in an elongated state and applying a stream of hot air to the strand with a hair dryer.

2. The process according to claim 1, wherein the temperature in step (d) is within the range of 90 to 110° C.

* * * * *